United States Patent [19] [11] Patent Number: 5,000,741
Kalt [45] Date of Patent: Mar. 19, 1991

[54] TRANSPARENT TRACHEOSTOMY TUBE DRESSING

[75] Inventor: Glenda G. Kalt, Boca Raton, Fla.

[73] Assignee: Kalt Medical Corporation, Fla.

[21] Appl. No.: 283,825

[22] Filed: Dec. 13, 1988

Related U.S. Application Data

[63] Continuation-in-part of Ser. No. 234,876, Aug. 22, 1988, Pat. No. 4,917,112, which is a continuation-in-part of Ser. No. 227,784, Aug. 3, 1988, Pat. No. 4,919,654.

[51] Int. Cl.⁵ .............................................. A61M 25/02
[52] U.S. Cl. ................................. 604/180; 604/307; 128/DIG. 26
[58] Field of Search .................. 604/174, 177–180, 604/305, 307, 308, 332, 338, 344; 128/DIG. 26, 207.14, 207.17, 887, 888

[56] References Cited

U.S. PATENT DOCUMENTS

| | | |
|---|---|---|
| 2,221,758 | 11/1940 | Elmquist . |
| 2,273,873 | 2/1942 | Klein . |
| 2,949,443 | 8/1960 | Merriam et al. . |
| 3,713,448 | 1/1973 | Arrott ........................ 128/DIG. 26 |
| 4,181,127 | 1/1980 | Linsky et al. . |
| 4,331,144 | 5/1982 | Wapner ....................... 128/DIG. 26 |
| 4,341,207 | 7/1982 | Steer et al. . |
| 4,341,208 | 7/1982 | Gordon . |
| 4,485,809 | 12/1984 | Dellas . |
| 4,678,467 | 7/1987 | Vaillancourt ............... 128/DIG. 26 |
| 4,699,616 | 10/1987 | Nowak et al. ............... 128/DIG. 26 |
| 4,744,355 | 5/1988 | Faasse, Jr. . |
| 4,838,878 | 6/1989 | Kalt et al. .................. 128/DIG. 26 |
| 4,917,112 | 4/1990 | Kalt ............................... 128/156 |
| 4,919,654 | 4/1990 | Kalt ................................ 604/180 |

FOREIGN PATENT DOCUMENTS 998901 10/1976 Canada .

OTHER PUBLICATIONS

The 3-M TEGADERM Transparent Dressing Brochure by the 3-M Company, 70-2008-23-85-7(87.3)BPH, ©1984.
Conmed Venigard Disposable Dressing brochures, Catalog Nos. 705-4431, 705-4432, and 745-1441, no date.

*Primary Examiner*—Stephen C. Pellegrino
*Assistant Examiner*—Ralph A. Lewis

[57] ABSTRACT

A transparent dressing for substantially sealing a wound consisting of a semi-rigid frame for defining an opening and a resilient transparent membrane member substantially covering the opening in order to form a transparent window. The transparent material allows air and vapors to permeate the material in a first direction and prevent contaminants and fluids from entering the wound area in an opposite direction. Several embodiments of the invention are shown for firmly holding tracheostomy tubes to the dressing.

14 Claims, 3 Drawing Sheets

TRANSPARENT TRACHEOSTOMY TUBE DRESSING

This application is a continuation-in-part of U.S. patent application Ser. No. 07/227,784, filed Aug. 3, 1988, now U.S. Pat. No. 4,919,654 and also is a continuation-in-part application of U.S. patent application Ser. No. 234,876, filed Aug. 22, 1988, now U.S. Pat. No. 4,917,112.

BACKGROUND OF THE INVENTION

The present invention relates in general to a tracheostomy tube dressing for covering the wound about a patient's neck such that the wound area can be covered while it is also allowed to heal.

Although opaque dressings have long been in use, their designs suffer from several drawbacks. First, the patient or person treating the patient has no idea how well the wound is healing until the dressing is entirely removed. Second, removal of the dressing increases the danger that the scab or skin covering the wound will be removed along with the dressing. Another drawback is that many dressings fail to adequately aerate the wound. In such instances, the healing of the wound is much slower. Another drawback of many conventional dressings is that part of the wound area is contacted by an adhesive portion of the dressing. Thus, when the dressing is removed, the tacky surface of the dressing will possibly harm the partially healed area.

These drawbacks are compounded in tracheostomy tube dressings where the dressing must serve the dual function of protecting the wound and holding the tracheostomy tube in place. Such a dressing must avoid the above drawbacks common to all dressings and still present a sufficiently rigid clamp for the tracheostomy tube.

To date, those transparent dressings and tracheostomy dressings that have been devised fail to avoid these drawbacks.

For example, the 3-M Corporation markets a transparent dressing under the trademarked name "TEGADERM" and the Johnson & Johnson Company sells a transparent dressing under the name "BIOCLUSIVE". Both dressings consist of a transparent air and vapor permeable film that have the surface of one side entirely coated with an adhesive. The dressings are supplied with releasable paper frames adhered to the non-adhesive side of each sheet. A paper frame is used in each dressing to maintain the integrity of the dressing's shape before it is applied to the patient's skin. Once applied, the frame is removed.

Although the "TEGADERM" and "BIOCLUSIVE" dressings are relatively simple in their construction, their adhesive surfaces may harm healing tissue when the dressings are removed. Another problem is that water or contaminants may seep into the wound site from the sides of the dressing due to the lack of a sealing frame.

The "TEGADERM" product also includes a design for use as a tracheostomy dressing. In this application, a slit is cut to extend from an edge of the dressing to the center. A center hole having the same diameter as a tracheostomy tube is then cut so that the slit contacts one side of the hole. The combination of the slit and center hole allow the bandage to be spread apart along the slit in order that a tracheostomy tube and cuff can easily slide into the center hole. When the slit is closed, the center hole surrounds the tube below the cuff and collar substantially enclosing the tube. However, the "TEGADERM" tracheostomy dressing does not contain a structure for securing the tracheostomy tube to the patient's neck. Instead, the tube is independently secured to a patient's neck by means of cloth ties which completely encircle the patient's neck. Thus, the cloth ties do not adequately hold the tube to the bandage. Movement of the ties or of the dressing will cause stress on the tube. The cloth ties also create a substantial risk of infection to patients having undergone recent surgery to the head and/or neck. Moreover, if the ties are made too tight, they can potentially choke the patient. The cloth ties are also susceptible to bacteria, creating a greater risk of infection around the puncture area for the tube. The cloth ties also create a substantial risk of infection to patients having undergone recent surgery to the head or neck. Finally, the cloth ties are inconvenient, requiring the treating nurse or physician to physically untie or retie a knot each time they wish to remove or adjust the tube.

Another transparent dressing is sold under the registered trademark "VENI-GARD" by the Conmed Corporation. "VENI-GARD" is a disposable dressing for holding an IV needle or catheter in a patient's vein. The "VENI-GARD" provides a sterile barrier over the puncture site and incorporates a transparent semi-permeable membrane material as the covering over the site. The purpose of the transparent membrane is to allow unobstructed visualization of the puncture locus while at the same time enabling the evaporation of any moisture that collects around the puncture site. However, the construction of the VENI-GARD dressing is complex. Further, the membrane is coated with an adhesive that renders the VENI-GARD unsuitable for use in covering a wound because the adhesive surface may harm the healing tissue when the dressing is removed.

Another example of a transparent dressing is shown in the Gordon patent, U.S. Pat. No. 4,341,208. The Gordon dressing has a transparent window and a flexible frame for adhering the window to the patient's skin. Thus, unlike "VENI-GARD," the Gordon dressing does not contact the adhesive layer to the wound. However, the material used with the window does not allow for the passage of air or moisture from the patient's skin to the exterior surface of the dressing. Moreover, the construction of the Gordon dressing requires a multiple layered window which employs an applicator layer adjacent to the transparent layer. The applicator spaces the window from the skin by the thickness of the frame which is not as sterile as an adjacent film because the spaced film traps air or other substances adjacent to the skin.

Another transparent dressing is illustrated by the Klein patent, U.S. Pat. No. 2,273,873. The Klein dressing involves a transparent adhesive sheet adapted to be used as a dressing for a wound. The wound is not sealed from outside contaminants since air passages are provided along portions of the frame of the dressing. In addition, the transparent material used in the Klein dressing is neither air nor vapor permeable, and the sheet does not contact the skin.

The Linsky et al. patent, U.S. Pat. No. 4,181,127, illustrates a non-adherent wound dressing employing an absorbent pad border that removes moisture from the area around the wound. A transparent film covers the wound and has its edges overlapped by an adhesive frame. However, the film is placed on top of the frame rather than below it, the materials of the frame are primarily webbing, and the film is an imperforate material that does not offer the advantages of a transparent air/vapor permeable barrier.

The Merriam et al. patent, U.S. Pat. No. 2,949,443, illustrates a water vapor permeable dressing applied directly to a surgical wound. The material of the dressing is primarily transparent and water and vapor permeable. However, the material is either applied to the skin through the use of an adhesive layer formed along the outer edge of the dressing, or through the application of an alcohol solvent applied to the skin directly. Such a construction does not adhere strongly to the patient's skin and may easily come loose from the wound area.

The Faasse, Jr. patent, U.S. Pat. No. 4,744,355, discloses a hinged releasable wound dressing in which a thin flexible polymeric film having an adhesive layer coated on one side of the dressing is applied directly to the site of the wound. The Faasse, Jr. dressing has the drawback of directly contacting the wound with adhesive which could cause the healing layer of skin to be pulled up when the dressing is removed.

Finally, the Dellas dressing illustrated in U.S. Pat. No. 4,485,809 provides for a transparent moisture vapor permeable film dressing. As in Faasse, Jr., the Dellas film also employs an adhesive in order to directly contact the dressing to the patient's skin. Therefore, the construction of the Dellas dressing can cause tearing of the partially healed wound when the dressing is removed from the patient's skin.

SUMMARY AND OBJECTS OF THE INVENTION

The present invention alleviates to a great extent the disadvantages presented by the prior art devices by providing for a transparent tracheostomy dressing of simple construction that completely seals a wound with a transparent gas/vapor permeable membrane, while avoiding contact between the dressing's adhesive surface and the wound. Moreover, the dressing secures the tracheostomy tube to the frame of the dressing such that the tube is firmly supported. The material of the transparent member is gas/vapor permeable only in the direction away from the wound such that outside contaminants cannot enter inside the dressing. The frame that adheres the transparent membrane to the wound is sufficiently rigid to adequately secure the tracheostomy tube yet sufficiently flexible so that the dressing can be comfortably worn while not folding over itself when applied to the skin.

The transparent dressing is substantially rectangular. The frame portion consists of a rectangular piece having a centrally defined opening. A similarly shaped but smaller rectangular transparent membrane is attached to the bottom of the frame such that a tacky adhesive border surrounds the transparent membrane. Two ties are adhered to opposing sides of the frame. The ties are oriented to loop around a tracheostomy tube located in the center of the rectangular opening. Moreover, a slit runs from one edge of the frame to the center of the transparent membrane. A center hole is formed out the center surrounded by a frame formed about the circumference of the center hole.

In another aspect of the invention, the dressing is substantially circular.

In still yet another embodiment of the invention, the dressing has a frame with two fingers at opposing ends of the frame. A transparent window is formed in the center of the frame.

It is an object of the invention to provide for a transparent dressing yielding to the foregoing advantages that effectively holds a tube against a patient's body.

It is still an additional object of the invention to provide for a transparent dressing where the dressing does not have to be removed in order for the patient to observe the site of the wound.

It is still a further object of the invention to provide for a dressing of simple construction having a frame consisting of a single piece of material.

It is still a further object of the invention to provide for a dressing yielding to the foregoing advantages and that can clamp to a variety of sizes of tubes and yield to any skin surfaces of the body.

It is still an object of the invention to provide for a dressing that securely clamps a tracheostomy tube to the neck of a patient without requiring the use of cloth ties.

These and other objects of the invention are accomplished by the present invention as described by the drawings and detailed description herein.

DETAILED DESCRIPTION OF THE PREFERRED EMBODIMENTS

As referred to herein, the inner surfaces of various component parts of the preferred embodiments of the present invention are those surfaces oriented towards the object to which the dressing is adhered. Similarly, the outer surfaces of the various component parts of the preferred embodiments are those surfaces oriented away from such an object. Such an object may be any kind that is used for transparent dressings but will most likely be a patient's skin, their clothing, hair, or the like. The description of the present invention is provided with reference to the applicant's U.S. patent application No. 07/234,876 filed Aug. 11, 1988, the disclosure of which is incorporated herein by reference.

Figure 2:
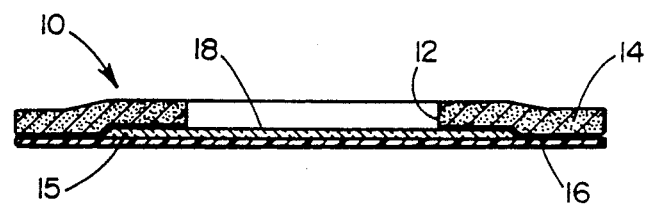
FIG. 2 is a cutaway view taken along section line II—II of FIG. 1.
Figure 1:
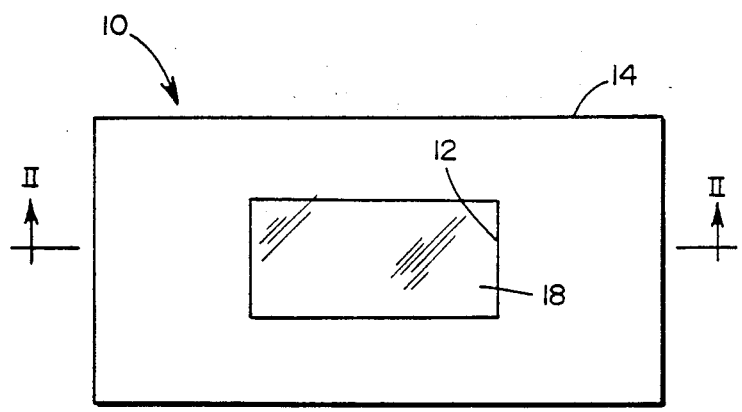
FIG. 1 is a top view of the first embodiment of a transparent dressing according to the present invention.
Figure 3:
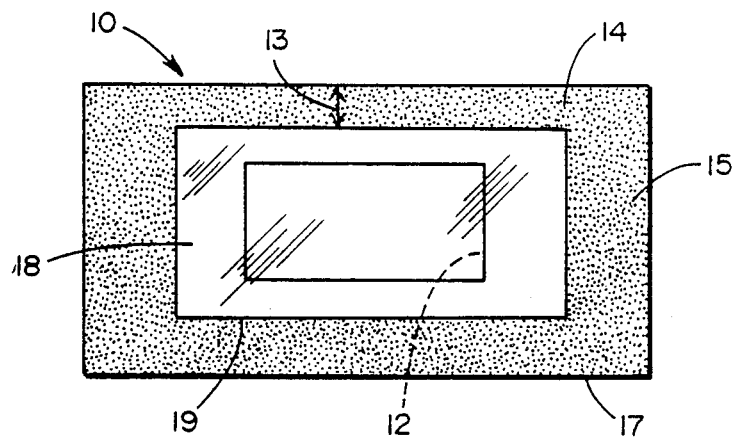
FIG. 3 is a bottom view of transparent dressing 10 of FIG. 1.

Referring now to the figures, wherein like parts are represented by like reference numerals, FIGS. 1-3 illustrate a first embodiment of the present invention designated by reference numeral 10. In the first embodiment, a transparent dressing 10 is shown. This embodiment is particularly suited for use in covering the wound of a medical patient. The transparent dressing 10 is designed such that it includes a centrally located opening 12. A frame surrounds the opening 12 creating a window at the center of the dressing 10.

The frame is preferably formed from a stretchable adhesive electrode foam material. Suitable materials for the frame include the adhesive foam marketed under the federal trademark "MACROLYTE" by the Conmed Company or marketed under the trademarked name, "MICROFOAM" by the 3-M Corporation. The advantages of such materials is that they are sufficiently flexible to be comfortably worn by the patient and sufficiently rigid to retain the shape of the dressing when it is not adhered to the patient's skin. Thus, the frame insures that the dressing will not fold upon itself during application or not retain its shape when packaged. Moreover, the foam material is substantially water-resistant, thus providing a barrier to contamination by bacteria or liquids.

While the shape of frame 14 is shown as being rectangular in FIGS. 1 through 3, it can be formed into any desired configuration. It is to be noted that by incorporating different shapes and sizes, the dressing can more effectively accommodate different parts of the body. Thus, different shapes would necessarily be contemplated by the present invention to cover elbows, knees, fingers, bony prominences or different objects such as tubes or the like. For example, it is contemplated that the frame can be substantially oval, triangular or formed into a fanciful design such as a star, fish or heart. Other shapes of the present invention are illustrated in the remaining figures.

Returning now to FIG. 1, the opening 12 is enclosed along the bottom side by a transparent membrane 18. The membrane is adhered to frame 14 in such a manner that it cannot easily separate during use.

The material of the membrane 18 is preferably a hypo-allergenic non-adhesive flexible plastic that allows vapor and gasses to escape through the material in one direction but blocks contaminants and moisture from coming into the material in a second direction. It is preferred that the material for membrane 18 is either "TEGADERM TM " marketed by the 3-M Corporation or "BIOCLUSIVE TM " marketed by the Johnson & Johnson Company. However, any other material having similar characteristics as described above can be employed.

The frame 14 is coated on its bottom surface with a medical grade adhesive, preferably a hypo-allergenic synthetic acrylic pressure sensitive adhesive. The adhesive is used to secure the membrane 18 to the frame 14 as well as to secure the frame 14 to the patient's skin. The acrylic adhesive is of sufficient tackiness to seal the wound from liquids or air seepage that may occur between the base of frame 14 and the patient's skin. The adhesive thus serves in combination with the frame to create a water tight barrier between the interior of the dressing and the exterior environment. However, the adhesive is sufficiently weak that the dressing 10 can be removed with a minimum of resistance.

FIG. 2 shows a cut-away view of a cross-section of dressing 10 taken along reference lines II—II of FIG. 1. The membrane 18 is substantially smaller in width than the width of frame 14. When frame 14 is adhered to the membrane 18 by means of adhesive layer 15, those portions of frame 14 that extend beyond the membrane serve as an adhesive border that is used to adhere the dressing 10 to the patient's skin. Although adhesive layer 15 is shown covering the entire bottom surface of frame 14, different types of adhesives can be used on different portions of frame 14. For example, a stronger adhesive can be employed to adhere the membrane 18 to the frame portion 14 while a weaker adhesive can be used along the adhesive border.

In a preferred embodiment, a liner 16 extends substantially across the adhesive border of frame 14 and the entire bottom surface of membrane 18 As shown, the liner 16 adheres against the membrane as a result of the tacky adhesive surface 15. By employing liner 16, the membrane 18 is protected and the adhesive surface 15 remains unexposed. In use, the liner 16 is peeled off of the frame 14 exposing the tacky adhesive surface for contact with a patient's skin. The materials of the liner can consist of any conventionally used paper or plastic liner.

FIG. 3 is a bottom view of the first embodiment illustrated in FIG. 1. More particularly, FIG. 3 shows the relationship between the membrane 18 and the frame 14. The perimeter 17 of the frame 14 is of such dimension that it is substantially wider and longer than the perimeter 19 of the membrane 18. The difference in perimeters defines a border area 13 formed around the membrane 18. As the adhesive material 15 covers the surface area of border 13, the border provides a complete adhesive frame around the non-adhesive bottom surface of the membrane 18. The wound area, which is primarily covered by the membrane 18, will thereby not contact adhesive surface 15.

Figure 4:
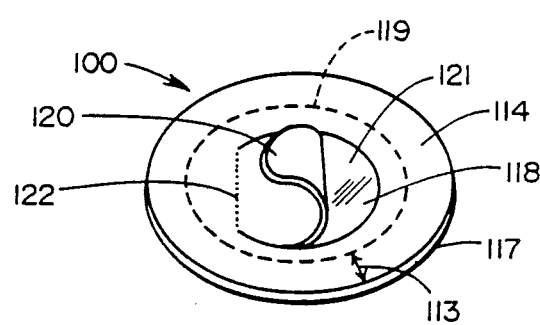
FIG. 4 is a perspective view of a second embodiment of a transparent dressing according to the present invention.

Referring now to FIG. 4, a second embodiment 100 consisting of a circular dressing, is shown. The dressing according to the second preferred embodiment of the invention is generally similar in construction to the first embodiment described in conjunction with FIGS. 1-4. One major difference between the first and the second embodiments, however, is flap 120 for covering the transparent opening 121.

The dressing 100 includes a frame 114 composed of a medical grade foam that is similar to that described for use with the first preferred embodiment. The base 114 is coated with a medical grade adhesive (not shown) along its bottom surface in order to adhere a transparent membrane to the frame and the frame to the patient's skin. The adhesive, in turn, can secure a circularly shaped membrane material 118 such that it surrounds and covers the opening 121. The circumference 119 of the membrane 118 is less than the circumference of frame 114. Thus, a border referenced by radial arrow 113 is defined by the differences in size of these two elements. As previously discussed, the tacky adhesive surface (not shown) on the border of frame 14 is employed to adhere the circular dressing 100 to the skin.

The dressing further includes a flap 120 which is formed integrally with the frame 114. As shown, the flap is configured to substantially fit within opening 121 to cover the surface of transparent membrane 118. In order to open the flap, it is folded back towards the frame along fold line 122.

Although the flap 120 is shown to be configured to fit within opening 121, alternate shapes and constructions can be used. For example, flap 120 can be shaped to extend beyond the edge of opening 121 (not shown). The advantage of this latter design is that a person can readily grip the edge of flap 120 extending beyond the opening 121. The material of the flap can also be modified so as to allow air/vapor passage out to the exterior of the dressing. Such materials can include, but not be limited to an opaque "TEGADERM" sheet having the same characteristics as membrane 18. Alternatively, the flap can be made of the same material as that of the frame 114 but can further include a plurality of air holes to allow air passage into and out of opening 121.

FIGS. 5a, 5b, 6a and 6b each illustrate tracheostomy tube holder embodiments 200 and 250 yielding many of the afore-described advantages described above in FIGS. 1-4.

Figure 5A:
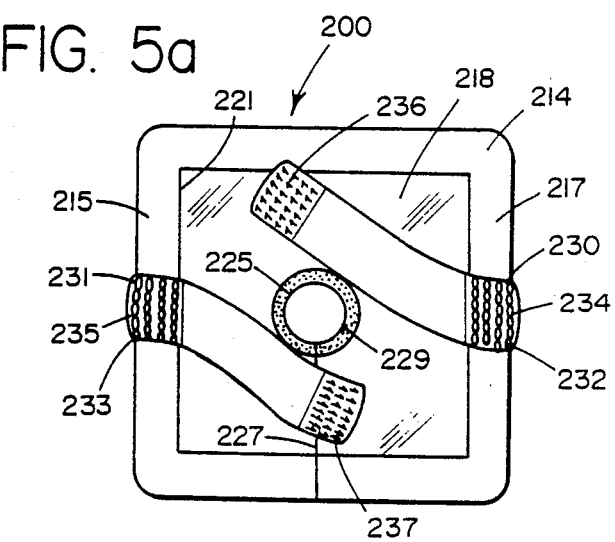
FIGS. 5a-5b are top views of a third embodiment and fourth embodiment of a transparent dressing according to the present invention.

The tracheostomy tube holder 200 shown in FIG. 5a includes a frame 214 formed from similar material to that described with reference to the first and second embodiments. The frame substantially surrounds an opening 221. As previously described, the opening is then covered by a transparent membrane portion 218 formed of a similar transparent material described above. Located at the center of the membrane 218 is a central tube hole 225 and a tube hole collar 229. The material of collar 229 is the same stretchable medical foam that forms frame 214. The collar 229 is attached to both the inner and outer surfaces of the membrane 218. Only the outer surface with upper collar 229 is shown. In addition, an adhesive layer is coated on the upper collar 229 and the lower collar below membrane 218 in order that the collars adhere both to the skin around the tracheostomy tube and to the cuff of the tube itself. A slit 227 extends through frame 214, membrane 218, and collar 229 to the tube hole 225. The slit enables the tracheostomy tube dressing 200 to sufficiently accommodate insertion of the tube into hole 225 and inside the collar 229. In addition to tracheostomy tubes, the dressing of FIG. 5a is adaptable for use as a stoma or fisula dressing.

A pair of tracheostomy tube ties 230, 231 are mounted on the sides 215, 217 of the frame 214 in a manner that they are generally oriented perpendicular to the longitudinal axis of the slit 227. Each tie is made of a flexible material that is adapted to substantially retain its shape under tension. Each tie respectively includes a first end 232, 233 having an inner surface that is coated with an adhesive layer (not shown). An outer surface of each first end consists of a loop fabric pad 234, 235, which is attached to the flexible material in any conventional manner. Each tie 230, 231 further includes a respective second end 236, 237, having a hook material also adhered to the tie 230, 231. The size and orientation of the tie material is designed to allow the tie to loop around a tracheal tube collar (see FIGS. 6a, 6b) in order that each second end 236, 237 of each tie respectively loops around the collar and mates with each respective first end 234, 235. The provision of ties 230, 231 enables a tracheostomy tube to be firmly held in place without placing any stress on a patient's neck or exposing the trachea wound to potential contaminants.

Figure 5B:
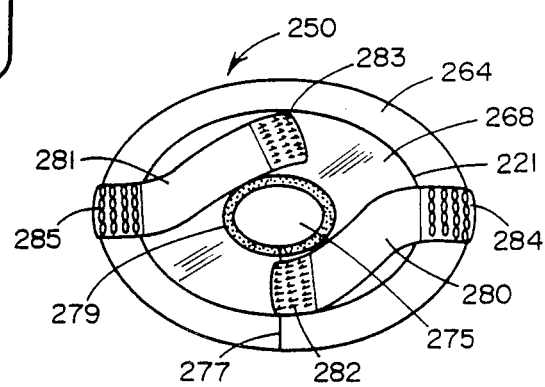

FIG. 5b illustrates a fourth embodiment of the present invention. As shown, an oval tracheostomy tube holder 250 includes a foam frame 264 formed of a similar material to that described above. The frame defines an opening 221 which is substantially covered by a vapor and gas permeable transparent membrane 268. An upper collar 279 made of a tacky foam material, in turn, surrounds the tube hole 275 centrally located in membrane 268. Moreover, a slit 277 is formed extending radially from tube hole 275 to the edge of frame 264. A pair of tracheostomy tube ties 280 and 281 are mounted on frame 264, as described above, such that ends 282, 283 are adapted to loop around a tube and respectively mate with ends 284, 285.

Figure 6A:
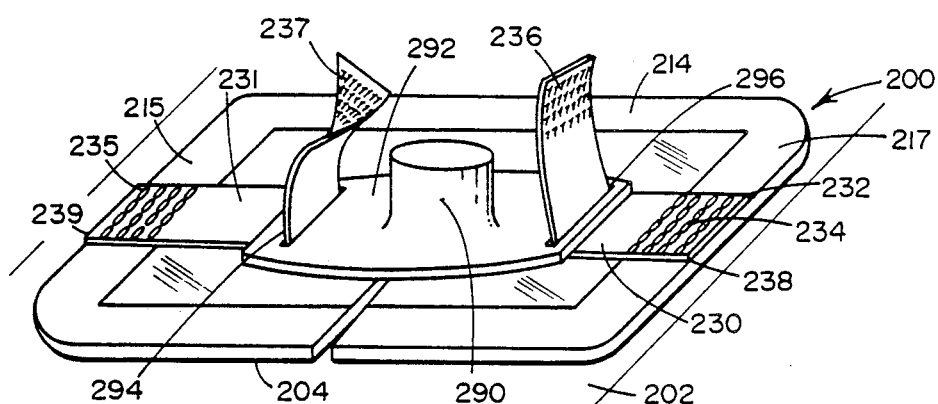
FIGS. 6a-6b are perspective views of the fifth embodiment of FIG. 5a in use.
Figure 6B:
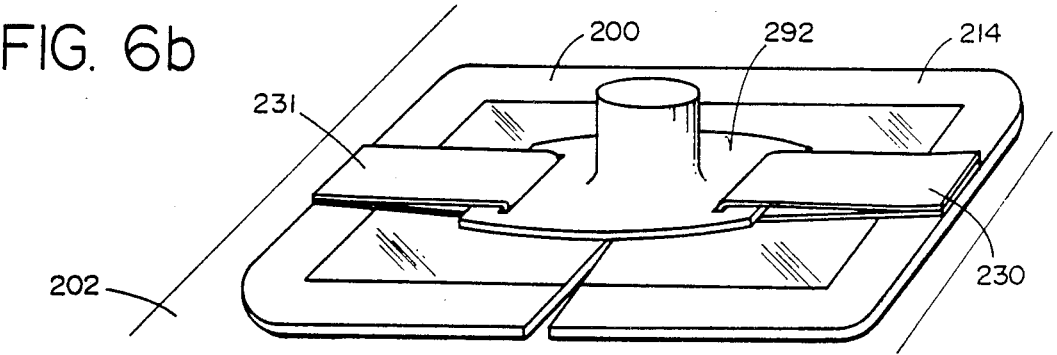

FIGS. 6a and 6b illustrate the fifth embodiment 200 in use. The tracheostomy tube holder 200 is adhered to a user's skin 202 by means of an adhesive layer 204 located on the inner surface of frame 214. A tracheostomy tube 290 is secured at its cuff (not shown) by a collar 292. The collar 292 includes slots 294 and 296 located at respective ends of the collar adjacent frame sides 215 and 217. The tracheostomy tube ties 230, 231 are adhered to sides 215 and 217 by an adhesive layer 238 and 239 located underneath each first end 234, 235 of each of the ties 230, 231. The ties 230, 231 are then looped through slots 294 and 296 in order that their respective second ends 236, 237 can fold back over the collar 292 and mate with respective first ends 232, 233.

A slit 227 opens the tube holder 200 to accommodate the curve of the patient's neck. The tube is held firmly to the dressing 200 by means of the adhesive collar 229 such that the skin around the tracheostomy tube is both visible and substantially covered by the membrane 218.

FIG. 6b shows the clamp 200 mounted on a patient's skin 202. The tube collar 292 is securely tied onto the frame 214 by means of ties 230, 231 in the manner described above.

Figure 7:
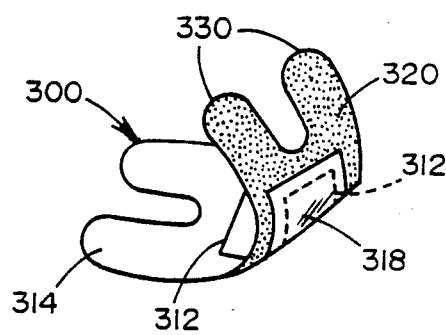
FIG. 7 is a perspective view of a sixth embodiment of the transparent dressing of the present invention.

FIG. 7 illustrates a sixth embodiment 300 of the transparent dressing suitable for special application over raised portions of a patient's body. The frame 314 is formed of a substantially similar stretchable foam material to that described above. However, the frame includes a pair of finger portions 330 located at opposed ends such that the overall "H" shaped frame is formed. The arrangement of membrane 318, opening 312 and adhesive border 320 are identical to that described in the first through fourth embodiments of the present invention.

Figure 8:
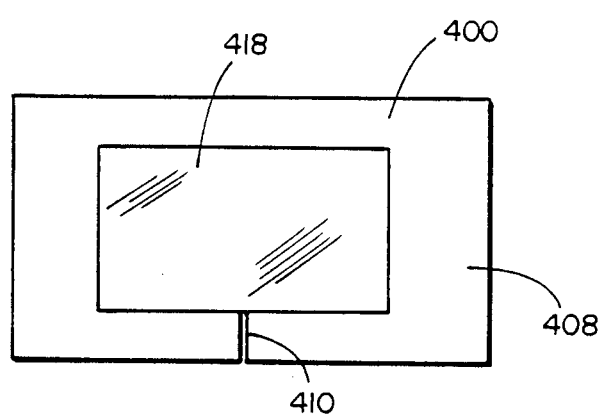
FIG. 8 is a top view of a seventh embodiment of the transparent dressing of the present invention.

FIG. 8 illustrates a seventh embodiment of the present invention 400. As shown, the construction of dressing 400 is identical to the first embodiment (FIG. 1) except for slit 410 along one side of frame 408. The dressing of FIG. 8 is useful for securing any tube or line that must enter a sterile field under the membrane 418. The dressing 400 is of particular importance for Hickman catheters, jugular intra-venous lines, central intravenous catheter dressings and gastrostomy tube dressings.

Figure 9A:
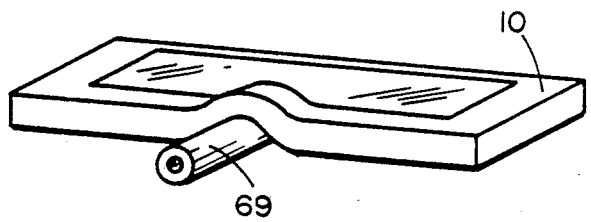
FIGS. 9a-9b are respectively perspective views of the first embodiment in use and the seventh embodiment in use.
Figure 9B:
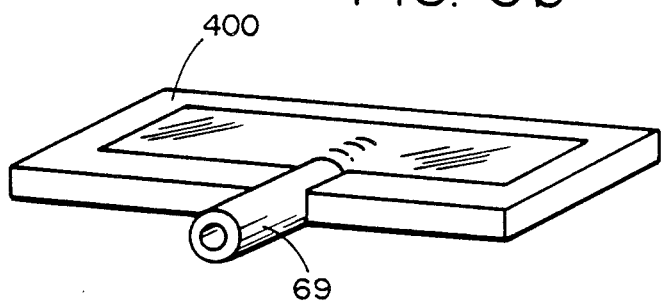

The slit 410 is incorporated into the frame 408 in order to prevent contaminants from entering the wound site. This is accomplished by using the slit 410 as the channel through which a tube 69 is inserted into the dressing as shown in FIG. 9b. When the tube 69 is placed in the slit, the slit closes along the sides of the tube, sealing the area around the tube 69 from contaminant/moisture seepage into the puncture site. Thus, the use of the slit avoids the drawback of having the dressing 10 lift up as shown in FIG. 9a around the edges of the tube 69. By keeping the wound site sterile, the infection potential about the wound is substantially decreased.

The dressings shown in the various embodiments of the present invention also have the advantage of maintaining an effective barrier to allow for the insertion of various medications and salves, without spillage. Such materials can be contained close to the wound while the dressing and its foam frame enables a patient to shower or even submerge the dressing without affecting such medications.

The dressing as described in the preferred embodiments is shown in use in a hospital setting. Although, as already pointed out, the dressing may be used in other settings both medical, and non-medical, for holding articles to objects or for securing and sealing objects.

For example, one such setting is in the electronics industry where transparent sealing devices may be used to secure wires within, around or between equipment. Another application is in shipping for holding labels to boxes, in dentistry for securing tubes to a patient's mouth, or in packaging for containing spoilable goods in a breathable package.

What is new and desired to be protected by Letters Patent of the United States is:

We claim:

1. A transparent dressing for a tracheostomy tube comprising:
   a frame having an opening substantially surrounded by said frame;
   a transparent non-adhesive membrane positioned below said frame and over said opening wherein a perimeter of said frame substantially surrounds said transparent membrane, said membrane having a central aperture for accommodating said tracheostomy tube through said aperture;
   an adhesive layer on a bottom surface of said frame such that said membrane is secured to a portion of said frame and said frame portion that extends beyond said membrane forms an adhesive border such that said transparent dressing is adhered to a patient's skin by said adhesive border; and
   a pair of ties each having a first end attached to said frame and a second end adapted to attach said tracheostomy tube extending through said central aperture to said frame.

2. The transparent dressing according to claim 1, wherein said frame is formed of a semi-rigid foam material.

3. The transparent dressing according to claim 2, wherein said transparent membrane consists of an air permeable flexible material such that said transparent dressing allows visual observation of tracheostomy wound.

4. The transparent dressing according to claim 2, further comprising a liner located below said membrane and attached to said adhesive border such that said liner is adapted to be peeled off of said adhesive border, exposing said adhesive border for contact with such patient's skin.

5. The transparent dressing according to claim 4, wherein said liner consists of a paper material.

6. The transparent dressing according to claim 1, wherein said frame and said transparent membrane are substantially rectangular.

7. The transparent dressing according to claim 1, wherein said frame, and said transparent membrane and opening are substantially circular.

8. The transparent dressing according to claim 1, wherein said central aperture contacts a slit that extends from one edge of said central aperture to an edge of said transparent dressing such that said central aperture can hold said tracheostomy tube to such skin while accommodating curvatures in a patient's neck and still prevent contaminants or liquid from entering a wound site.

9. The transparent dressing according to claim 8, further comprising a semi-rigid flexible collar surrounding said tube hole and located on the top and bottom surfaces of said transparent membrane.

10. The transparent dressing according to claim 9, wherein said collar comprises a top collar member located above all transparent membrane and a bottom collar member located below said transparent membrane whereby said top and bottom collar members have respective adhesive surfaces enabling said collar members to be adhered to said top and bottom surfaces of said transparent membrane, to a patient's skin and to said tracheostomy tube.

11. The transparent dressing according to claim 10, wherein said first end of each of said ties includes a loop material and said second end of each of said ties includes a hook material whereby a respective second end is adapted to mate with a respective first end of each of said ties.

12. The transparent dressing according to claim 11, wherein each of said second ends is adapted to loop through a slit located on said tracheostomy tube and back toward said respective first end of each of said tie thus firmly securing said tracheostomy tube to said transparent dressing.

13. A dressing for a tube, comprising:
   a frame member surrounding a window;
   a transparent membrane attached to said frame member, and covering said window and having a tube opening for accommodating a tracheostomy tube;
   an adhesive border formed on said frame around the perimeter of said transparent membrane such that when adhered to a patient's skin, a chosen area of such skin shows through said membrane covered window opening; and
   a pair of ties attached to said frame member wherein each of said ties is adapted to secure said tube to said frame thereby holding said tube in place in said tube opening.

14. The dressing according to claim 13, wherein said frame member incorporates a slit extending from said tube opening to an end of said frame member to prevent lifting up of said dressing when said tube is inserted into said dressing and to insure said dressing is sealed around said tube such that contaminants and fluids are prevented from entering said dressing.

* * * * *